US010371662B2

(12) United States Patent
Uemura (10) Patent No.: US 10,371,662 B2
(45) Date of Patent: Aug. 6, 2019

(54) CONTROLLER OF AIR-FUEL RATIO SENSOR

(71) Applicant: DENSO CORPORATION, Kariya, Aichi-pref. (JP)

(72) Inventor: Shinya Uemura, Kariya (JP)

(73) Assignee: DENSO CORPORATION, Kariya (JP)

( * ) Notice: Subject to any disclaimer, the term of this patent is extended or adjusted under 35 U.S.C. 154(b) by 301 days.

(21) Appl. No.: 15/249,588

(22) Filed: Aug. 29, 2016

(65) Prior Publication Data

US 2017/0067798 A1   Mar. 9, 2017

(30) Foreign Application Priority Data

Sep. 9, 2015  (JP) ................................. 2015-177600

(51) Int. Cl.
*G01M 15/10* (2006.01)
*G01N 27/406* (2006.01)

(52) U.S. Cl.
CPC .............................. *G01N 27/4065* (2013.01)

(58) Field of Classification Search
CPC ............ G01N 27/4065; F02D 41/1454; F02D 41/2454; F02D 41/1495; F01N 11/007; H02M 2001/0009
USPC ....... 60/285; 701/103; 702/24, 104; 73/1.88, 73/204.14, 204.15
See application file for complete search history.

(56) References Cited

U.S. PATENT DOCUMENTS

| 4,307,450 A * | 12/1981 | Carp ..................... F02D 41/266 123/696 |
| 4,681,077 A * | 7/1987 | Kobayashi .......... F02D 41/1487 123/686 |
| 5,265,458 A * | 11/1993 | Usami .................. G01N 27/419 204/406 |
| 5,908,463 A * | 6/1999 | Akazaki ................ F02D 41/008 123/480 |
| 6,468,478 B1 * | 10/2002 | Honda ............... G01N 27/4175 324/717 |
| 2001/0000956 A1 * | 5/2001 | Honda ............... G01N 27/4067 338/34 |
| 2002/0162743 A1 * | 11/2002 | Inagaki .............. G01N 27/4065 204/425 |
| 2004/0051510 A1 * | 3/2004 | Saggini ................. H02M 3/157 323/282 |
| 2005/0000810 A1 * | 1/2005 | Tashiro ............... F02D 41/1454 204/424 |

(Continued)

FOREIGN PATENT DOCUMENTS

JP        H11-230931 A     8/1999

*Primary Examiner* — John E Breene
*Assistant Examiner* — Jeffrey P Aiello
(74) *Attorney, Agent, or Firm* — Posz Law Group, PLC (57) ABSTRACT

A controller of an air-fuel ratio sensor includes, in a digital processor, an adjuster and a control unit, among which the adjuster adjusts a second input digital value for a control of an output voltage of a second voltage application circuit to a preset voltage, and the control unit controls, based on a calculation result of a digital value of a sensor current, a first input digital value for a control of an output voltage of an output terminal of a first OP amplifier of a first voltage application circuit to a voltage Vu based on the equation, $Vu=Vout\pm(Vtar+Is\times Rs)$, so that an application voltage applied to the air-fuel ratio sensor is quickly adjusted to a target voltage.

5 Claims, 11 Drawing Sheets

(56) References Cited

U.S. PATENT DOCUMENTS

| | | | | |
|---|---|---|---|---|
| 2005/0127899 A1* | 6/2005 | Kakuta | .................... | G01D 5/14 |
| | | | | 324/207.2 |
| 2005/0217347 A1* | 10/2005 | Kawase | ............. | G01N 27/4175 |
| | | | | 73/23.31 |
| 2010/0031941 A1* | 2/2010 | Hokuto | ............... | F02D 41/0025 |
| | | | | 123/575 |
| 2015/0323493 A1* | 11/2015 | Uemura | ................. | F02D 41/28 |
| | | | | 204/406 |

* cited by examiner

CONTROLLER OF AIR-FUEL RATIO SENSOR

CROSS REFERENCE TO RELATED APPLICATION

The present application is based on and claims the benefit of priority of Japanese Patent Application No. 2015-177600, filed on Sep. 9, 2015, the disclosure of which is incorporated herein by reference.

TECHNICAL FIELD

The present disclosure generally relates to an air-fuel ratio sensor.

BACKGROUND INFORMATION

The air-fuel ratio sensor is a sensor that is provided for a detection of the exhaust gas of the internal-combustion engine, and for a control of the air-fuel ratio of a fuel-air mixture that is supplied to the internal-combustion engine to a desired value, which outputs a detection signal that changes according to the density of the exhaust gas.

Generally, when the detected density of the exhaust gas is a stoichiometric value (i.e., a theoretical air-fuel ratio), the electric current in the sensor is equal to 0 [A], with a bi-directional flow of the electric current flowing therein according to a rich and lean state of the combustion.

For example, a current sensing resistor is used for detection of (i.e., to sense) a sensor current that flows in the air-fuel ratio sensor, and a fuel injection control is appropriately performed based on a detected voltage between the terminals of the current sensing resistor in which the sensor current flows.

An example of a controller of the air-fuel ratio sensor is shown in a patent document, JP H11-230931 A (patent document 1) as an air-fuel ratio sensing device. In the art of the patent document 1, an electric current is provided from each of the two operational amplifiers, i.e., respectively from the output terminals, to each of the terminals of the air-fuel ratio sensor via the resistors, for an application of a voltage to each of the two terminals of the air-fuel ratio sensor.

According to the method of the patent document 1, for a feedback of the voltage of the sensor element, a feedback resistor is provided at a position between the output terminal of a drive circuit and the inverted input terminal of the operational amplifier, and an electric current flowing in the sensor element is detected by the current sensing resistor, and the voltage and the electric current output from the two operational amplifiers are controlled based on the detected voltage.

However, in such a configuration, it takes time for the application voltage applied to the sensor element to have a stable voltage value, which is not preferable. Further, even when a capacitor element is connected to the above-mentioned feedback resistor for a phase compensation, it still takes time to control. i.e., to adjust, the application voltage to a target voltage value.

SUMMARY

It is an object of the present disclosure is to provide a controller of the air-fuel ratio sensor, which is capable of controlling the application voltage applied to the air-fuel ratio sensor as quickly as possible to a target voltage value.

In one aspect of the present disclosure, a controller of an air-fuel ratio sensor for controlling an application voltage applied to a first and second terminal of the air-fuel ratio sensor includes a first voltage application circuit having a first Digital-to-Analog converter that converts a first input digital value input to the D/A converter as an instruction value to an analog value, and a first operational (OP) amplifier (i) receiving an analog output voltage from the first D/A converter by an non-inverted input terminal, and (ii) connecting an output terminal of the first OP amplifier to an inverted input terminal, and applying an output voltage of the output terminal of the first OP amplifier to the first terminal of the air-fuel ratio sensor. The controller also includes a second voltage application circuit having a second D/A converter that converts a second input digital value input to the D/A converter as an instruction value to an analog value and a second operational (OP) amplifier (i) receiving an analog output voltage from the second D/A converter by an non-inverted input terminal and (ii) connecting an output terminal of the second OP amplifier to an inverted input terminal, and applying an output voltage of the output terminal of the second OP amplifier to the second terminal of the air-fuel ratio sensor. The controller further includes a current sensing resistor being disposed at a position in a voltage application path to the air-fuel ratio sensor between the output terminal of the first OP amplifier of the first voltage application circuit, and the output terminal of the second OP amplifier of the second voltage application circuit, the current sensing resistor sensing a sensor current (Is) that flows in the air-fuel ratio sensor. The controller also includes an Analog-to-Digital (A/D) converter converting a detected voltage that is detected by the current sensing resistor by an A/D conversion and outputting a digital value, and a digital processor outputting, as the instruction value, (i) the first input digital value for the first D/A converter and (ii) the second input digital value for the second D/A converter, based on the digital value from the A/D converter. The digital processor includes an adjuster adjusting the second input digital value for a control of the output voltage of the second voltage input circuit to a preset voltage, a calculator calculating a digital value of the sensor current flowing in the current sensing resistor based on a ratio of the output digital value of the A/D converter against the resistance value of the current sensing resistor, and a control unit controlling the first input digital value based on a calculation result of the calculator, to control the output voltage of the output terminal of the first OP amplifier of the first voltage application circuit as a voltage Vu based on an equation, $Vu=Vout±(Vtar+Is×Rs)$. A term Vtar is a target voltage applied to the air-fuel ratio sensor, and a term Is is the sensor current, and a term Rs is a resistance value of the current sensing resistor. An adjusting factor $(Vtar+Is×Rs)$ is added to the voltage Vout according to a plus sign of "±" in $Vout±(Vtar+Is×Rs)$, in a first situation where (i) the output voltage of the first voltage application circuit is applied to the first terminal on an upstream side of the air-fuel ratio sensor, and (ii) the output voltage of the second voltage application circuit is applied to the second terminal on a downstream of the air-fuel ratio sensor. Also, an adjusting factor $(Vtar+Is×Rs)$ is subtracted from the voltage Vout according to a minus sign of "±" in $Vout±(Vtar+Is×Rs)$, in a second situation where (iii) the output voltage of the first voltage application circuit is applied to the second terminal on the downstream of the air-fuel ratio sensor, and (iv) the output voltage of the second voltage application circuit is applied to the first terminal on the upstream of the air-fuel ratio sensor.

In such manner, the target voltage is controllable by using a digital calculation process, and the application voltage applied to the air-fuel ratio sensor is controlled to the target voltage as quickly as possible.

BRIEF DESCRIPTION OF THE DRAWINGS

Objects, features, and advantages of the present disclosure will become more apparent from the following detailed description made with reference to the accompanying drawings, in which.

DETAILED DESCRIPTION

Hereafter, with reference to the drawings, embodiments of the controller of the air-fuel ratio sensor are described. In the following description, the same or similar numerals are assigned to the same or similar configuration in each of the embodiments, and the description of the same or similar configuration is not repeated in the second and subsequent embodiments.

First Embodiment

The first embodiment of the present disclosure is explained with reference to FIGS. 1 to 4.

Figure 1:
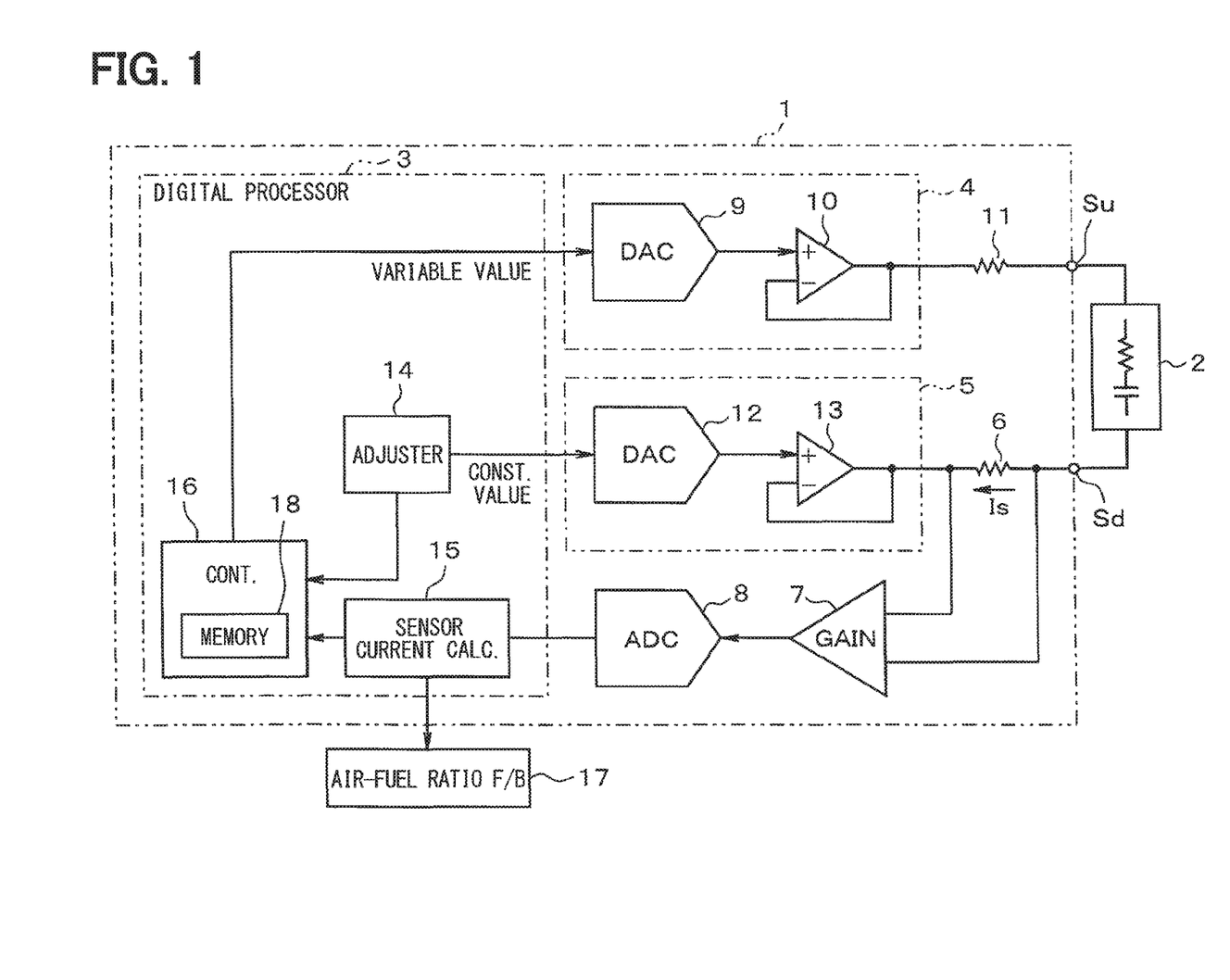
FIG. 1 is a block diagram of a controller of an air-fuel ratio sensor concerning a first embodiment of the present disclosure.

The electric configuration of a controller 1 of the air-fuel ratio sensor is shown in FIG. 1 as a block diagram.

The controller 1 in FIG. 1 is a device for controlling an air-fuel ratio sensor 2, i.e., for performing various control processes for the control of the sensor 2 that detects a density of oxygen in the exhaust gas from the internal-combustion engine used in a vehicle (not illustrated) and determines an air-fuel ratio.

The controller 1 is implemented as an Application Specific Integrated Circuit (ASIC), i.e., an Integrated Circuit (IC) dedicated for a specific application, for example, and includes a digital processor 3, a first voltage application circuit 4, a second voltage application circuit 5, a current sensing resistor 6, an amplifier 7, and an Analog-to-Digital (A/D) converter 8.

The first voltage application circuit 4 is provided with a first (Digital-to-Analog) (D/A) converter 9 and a first operational amplifier 10.

The first D/A converter 9 receives an input, i.e., an input digital value, from the digital processor 3 as an instruction value, and performs an analog conversion.

The first operational amplifier 10 is implemented as a so-called voltage follower circuit that (i) receives an input, i.e., an output analog voltage, from the first D/A converter 9 by a non-inverted input terminal and (ii) connects an output terminal to an inverted input terminal.

The output terminal of the first operational amplifier 10 is provided for an output terminal Su on an upstream side of the controller 1 via a resistor 11 that protects the first operational amplifier 10. That is, one terminal on an upstream side of the air-fuel ratio sensor 2 is connected to the output terminal Su on an upstream side of the controller 1.

The second voltage application circuit 5 is provided with a second D/A converter 12 and a second operational amplifier 13.

The second D/A converter 12 receives an input, i.e., an input digital value, from the digital processor 3 as an instruction value, and performs an analog conversion.

The second operational amplifier 13 is implemented as a so-called voltage follower circuit that (i) receives an input, i.e., an output analog voltage, from the second D/A converter 12 by a non-inverted input terminal and (ii) connects an output terminal to an inverted input terminal.

The output terminal of the second operational amplifier 13 is provided for an output terminal Sd on a downstream side of the controller 1 via the current sensing resistor 6. That is, the other terminal on a downstream side of the air-fuel ratio sensor 2 is connected to the output terminal Sd on the downstream side of the controller 1.

The current sensing resistor 6 is provided interposingly in a voltage application path for applying a voltage to the air-fuel ratio sensor 2, and the voltage application path connects the output terminal of the first operational amplifier 10 of the first voltage application circuit 4 and the output terminal of the second operational amplifier 13 of the second voltage application circuit 5. In the present embodiment, the current sensing resistor 6 is series-connected at a position between the output terminal of the second operational amplifier 13 and the output terminal Sd on the downstream side of the sensor 2. The current sensing resistor 6 is configured to detect, or to sense, an electric current that flows in the air-fuel ratio sensor 2 as a sensor current.

The A/D converter 8 performs an A/D-conversion process of the detection voltage detected by the current sensing resistor 6, and outputs a digital value. The digital value is inputted to the digital processor 3.

The digital processor 3 is configured so that the input digital value to the first D/A converter 9 and to the second D/A converter 12 is outputted therefrom as an instruction value based on the digital value of the A/D converter 8.

The digital processor 3 is implemented as a Digital Signal Processor (DSP), for example, and, is functionally provided as a combination of an adjuster 14, a calculator 15 of the sensor current, and the control unit 16.

The adjuster 14 sets a second input digital value inputted to the second D/A converter 12 as a constant value so that an output voltage of the second voltage application circuit 5 is adjusted to a preset voltage Vout (=Vsd). The constant value is inputted also to the control unit 16.

The calculator 15 calculates the digital value of the sensor current that flows in the current sensing resistor 6 based on a value derived from a division of the output digital value from the A/D converter 8 by the resistance of the current sensing resistor 6.

In the present embodiment, since the amplifier 7 is disposed at an interposing position between the current sensing resistor 6 and the A/D converter 8, the sensor current is calculable by the following equation (2). In the equation (2). Is is a sensor current, Vs is an output digital value of the A/D converter 8, Rd is a resistance of the resistor 6 for current detection, and G is an amplification rate of the amplifier 7. In the present embodiment, the resistance Rd of the resistor 6 is the same value as the resistance Rs of the current sensing resistor.

$$Is=Vs/(G \times Rd) \qquad \text{Equation (2)}$$

The calculator 15 provides the calculated sensor current Is as a feedback output 17 of the air-fuel ratio (to the other device), and also provides the calculated sensor current Is to the control unit 16. The control unit 16 is provided with a memory 18, and outputs, as an instruction value, the first input digital value of the first D/A converter 9 based on a calculated result of the constant value inputted from the adjuster 14 and the digital value of the sensor current Is from the calculator 15.

When a target voltage to be applied to the air-fuel ratio sensor 2 is designated as Vtar, the control unit 16 calculates an output voltage Vu of the first D/A converter 9 (which is substantially similar to the output voltage of the output terminal of the first OP amplifier 10) according to the following equation (1a), and controls the first input digital value of the first D/A converter 9 to correspond to the output voltage Vu. In the present embodiment, the resistance Ru of the resistor 11 is set to a resistance Rp of the protection resistor.

$$Vu=Vout+\{Vtar+Is \times (Ru+Rd)\} \qquad \text{Equation (1a)}$$

Figure 2:
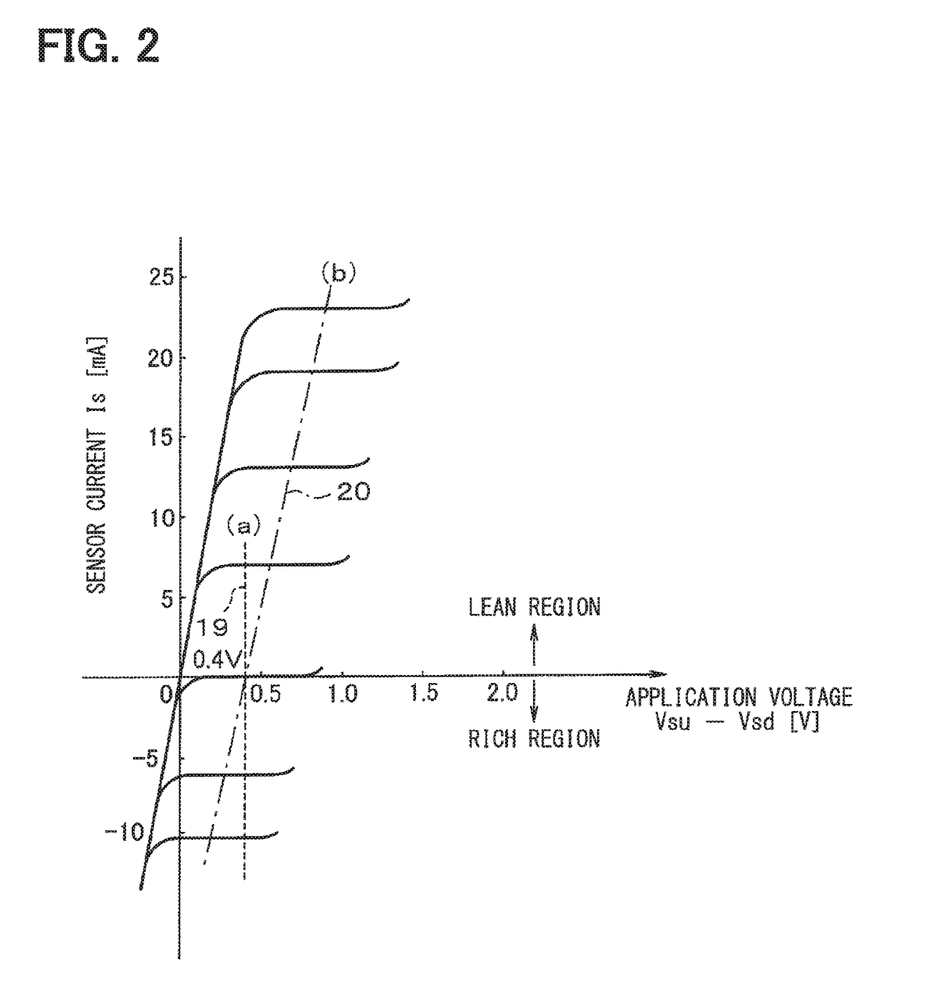
FIG. 2 is a diagram of an application voltage characteristic of a sensor current in the first embodiment of the present disclosure.

The change, i.e., an increase and a decrease, of the element current of the air-fuel ratio sensor 2 corresponds to the change of the air-fuel ratio (i.e., lean/rich). FIG. 2 shows an application voltage characteristic of the air-fuel ratio sensor 2 against the element (i.e., sensor) current Is, i.e., a graph of the sensor current Is [mA] versus the application voltage Vsu–Vsd [V].

As shown in the FIG. 2, when the air-fuel ratio becomes lean, the element current takes a positive value, for example, and, when the air-fuel ratio becomes rich, the element current takes a negative value. In the present embodiment, the target voltage Vtar is controlled to a preset voltage. Therefore, the application voltage applied to the air-fuel ratio sensor 2 takes a value along a load line 19, i.e., a line (a) in FIG. 2. The sensor current Is does not change, or changes little, by the change of the application voltage Vsu–Vsd, at a portion where the load line 19 crosses the graph of the sensor current Is. Thereby, the air-fuel ratio sensor 2 is used in a characteristic area where the transition of the sensor current Is is stable against the change of the application voltage Vsu–Vsd.

The operation of the controller 1 is described with reference to FIG. 3 in connection with the feature of the present embodiment based on the above-mentioned composition.

According to the present embodiment, even when the electric current that flows in the air-fuel ratio sensor 2 changes, the application voltage to the air-fuel ratio sensor 2 is controlled to the target voltage as quickly as possible, which is a feature of the control, or a feature of the controller 1. Thus, the following description focuses on a point how such a control is performed especially at the change timing of the sensor current Is.

During a normal operation time, based on an assumption that the air-fuel ratio is taking a stoichiometric value (i.e., a theoretical air-fuel ratio), the electric current that flows in the air-fuel ratio sensor 2 is 0 [mA], and the sensor current Is also becomes 0 [mA].

The digital processor 3 calculates the sensor current Is at the edge generation timing (e.g., at a falling timing) of the clock signal, and controls the application voltage to the air-fuel ratio sensor 2 immediately after the calculation of the sensor current Is. The sensor current calculation process and the application voltage control process are respectively performed at every edge generation timing of the clock signal.

During a period T1, the sensor current Is stays at 0 [mA], i.e., does not change. In other words, the change of the sensor current Is is 0. During such period, even though the calculator 15 of the digital processor 3 calculates the sensor current Is and the control unit 16 controls the application voltage, the application voltage Vsu to the output terminal Su is put to, i.e., is not changed from, a preset voltage Vu0 (e.g., 2.9 [V]), and the application voltage Vsd to the output terminal Sd is put to, i.e., is not changed from, a voltage Vd0 (e.g., 2.5 [V]).

During such time, the control unit 16 of the digital processor 3 controls the first input digital value as a constant value so that the output voltage Vsu outputted to the terminal Su through the first D/A converter 9 is controlled as a constant value.

Further, the control unit 16 of the digital processor 3 controls the second input digital value as a constant value so that the output voltage Vd of the second D/A converter 12 is controlled as a constant value.

Thereby, the application voltage Vsu–Vsd to the air-fuel ratio sensor 2 is controlled to the target voltage, i.e., to a constant voltage Vu0–Vd0.

For example, at a certain timing T2, under an influence of unknown factor (e.g., environmental temperature change), a change ΔI is caused in the sensor current Is, which may either be a positive value or a negative value (i.e., the change ΔI is assumed to be a positive value in the following description). When the sensor current Is changes at timing T2, the change ΔI will influence the voltage drop of the resistor 6, and the terminal voltage Vsd of the terminal Sd will change to Vd0+Rd×I under the influence of the voltage drop.

The change ΔI of the sensor current Is will also influence the voltage drop of the resistor 11 on the upstream side, and the terminal voltage Vsu of the terminal Su changes to Vu0−Ru×I under the influence at timing T2.

Then, the control unit 16 of the digital processor 3, upon detecting a change of the sensor current Is calculated by the calculator 15, raises, i.e., causes an upward change of, the application voltage Vu on the upstream side at the next clock timing T3.

At timing T3, as shown in the above-mentioned equation (1a), the upward change of the application voltage Vu on the upstream side is performed by an amount of I×(Ru+Rd).

Thereby, in consideration of the influence of the voltage drop of the resistor 11, the application voltage Vsu to the terminal Su on the upstream side is changed to Vu0+Rd×I.

As a result, the application voltage Vsu−Vsd to the air-fuel ratio sensor 2 is controllable to the constant voltage Vu0−Vd0.

Figure 3:
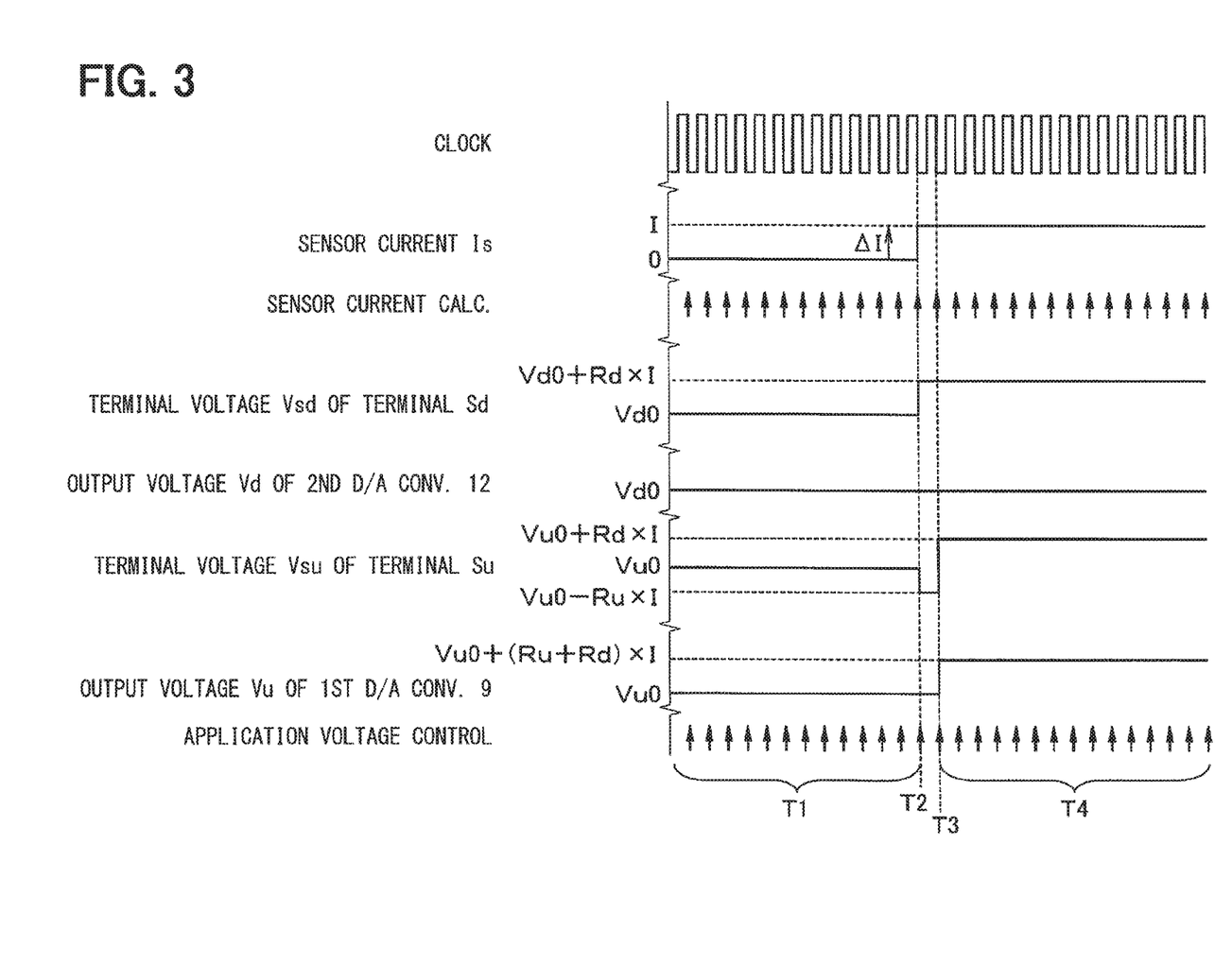
FIG. 3 is a timing chart of an operation of the controller in the first embodiment of the present disclosure.

Thereafter, as shown in FIG. 3 during a period T4, the control unit 16 maintains the application voltage Vsu if the sensor current Is does not change from the current value I.

DESCRIPTION OF COMPARATIVE EXAMPLE

Figure 4:
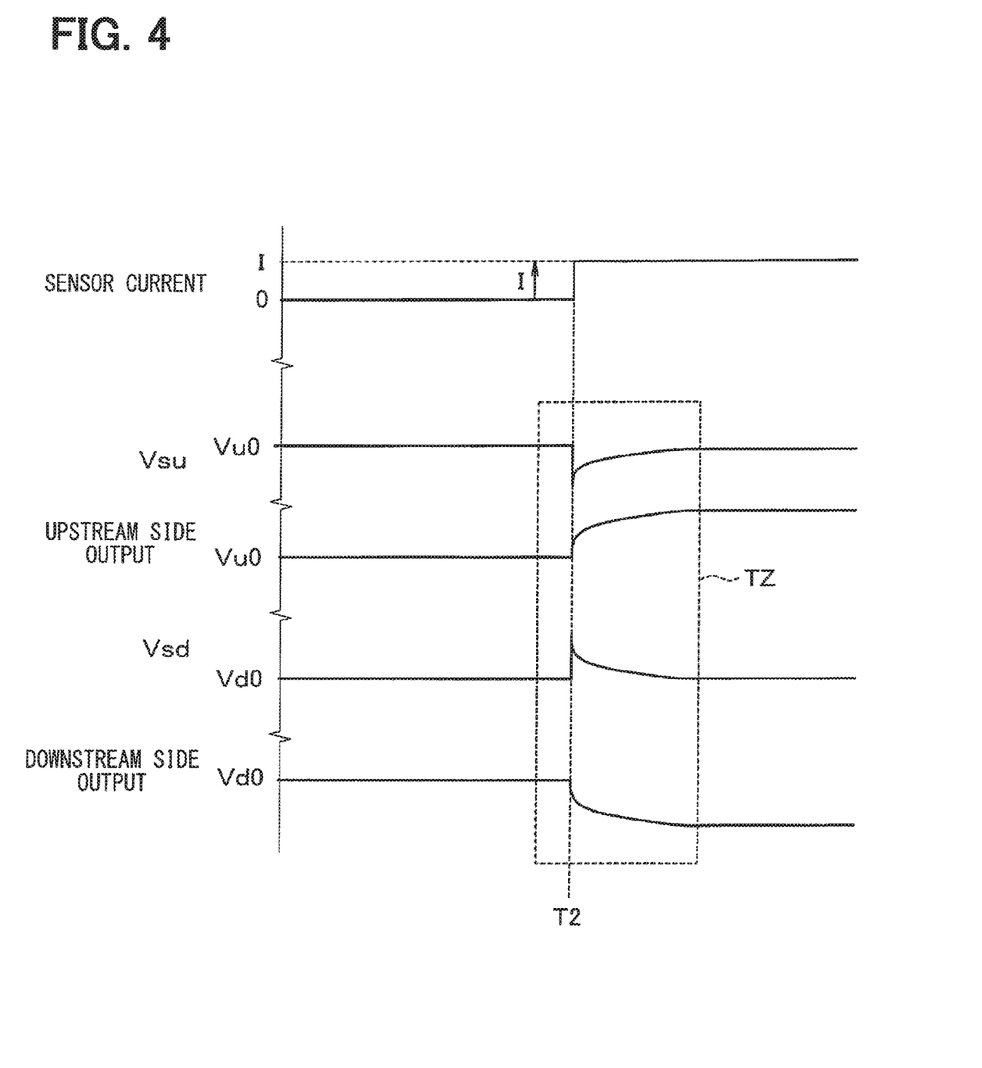
FIG. 4 is a timing chart of an operation of a comparative example.

FIG. 4 shows an operation, i.e., a timing chart, of an example that is provided as a comparison object.

For example, when the technique of the patent document 1 is used, at a steep change time of the element current that flows in the air-fuel ratio sensor 2 at timing T2, an analog control is performed. Therefore, as shown in a portion TZ of FIG. 4, the change of the application voltage to the air-fuel ratio sensor 2 is mitigated, or is slowed, causing a wait period of certain amount, i.e., delaying the stable operation for a long time.

SUMMARY OF THE PRESENT EMBODIMENT

In comparison, according to the present embodiment, based on a digital control performed by the digital processor 3, the output voltage to the terminals Su. Sd is controlled by the voltage follower circuit that is made up from the first and second D/A converters 9, 12 and the first and second operational amplifiers 10, 13. In such manner, the application voltages Vsu, Vsd applied to the terminals Su, Sd are controlled with high resolution.

Thus, even when the change ΔI in the sensor current Is of the air-fuel ratio sensor 2 is a very small change, a control for compensating the very small change ΔI is immediately performed, and the application voltage Vsu−Vsd applied to the air-fuel ratio sensor 2 is immediately controlled to the constant voltage Vu0−Vd0.

As a result, the application voltage to the air-fuel ratio sensor 2 is controlled to the target voltage Vtar without delay, i.e., as quickly as possible.

Since such a control is realized by the digital control of the digital processor 3, a manufacturing cost of the controlled is low as compared with an analog feedback configuration that requires a more complex structure than the digital feedback.

Second Embodiment

Figure 5:
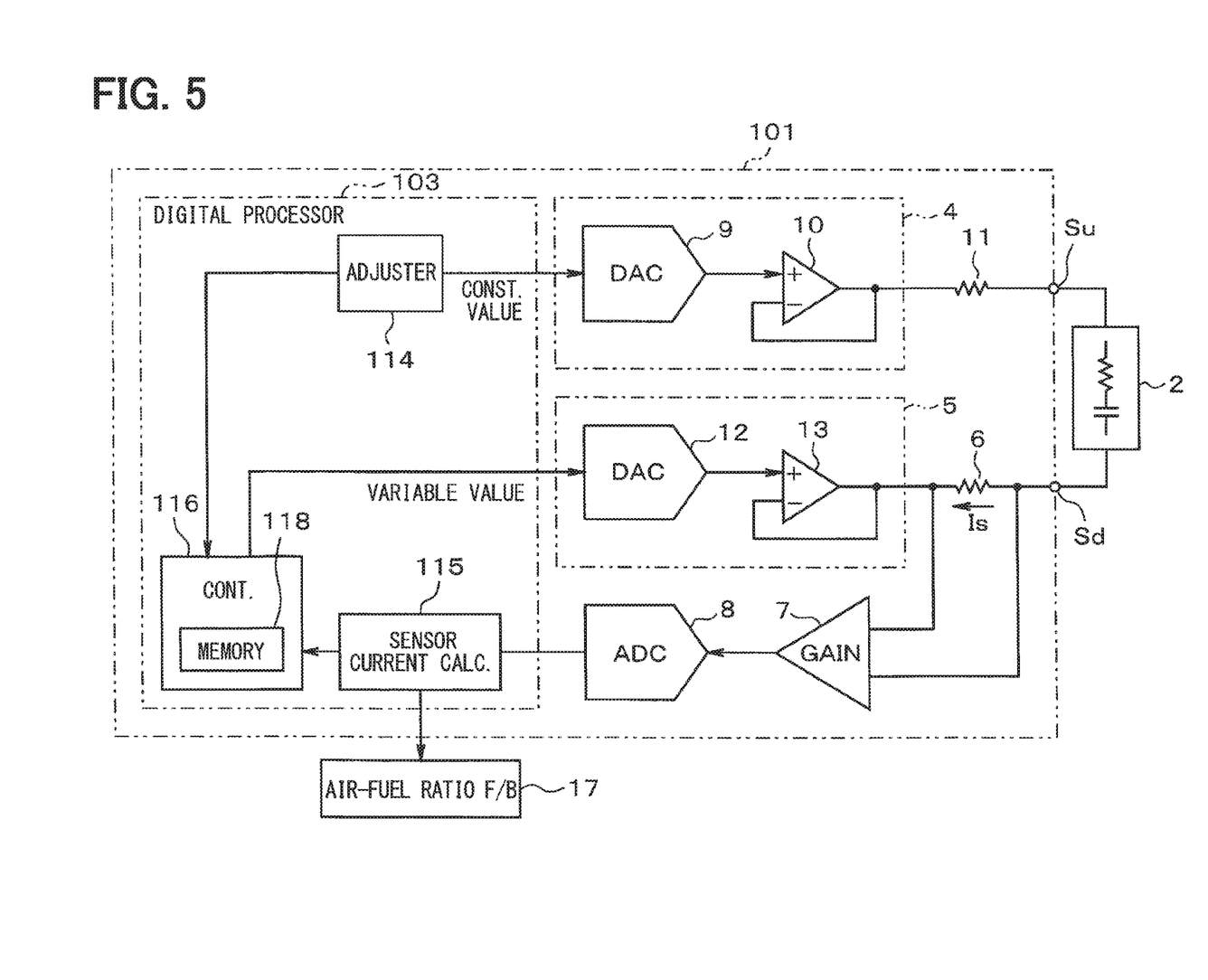
FIG. 5 is a block diagram of an electric configuration of the controller of the air-fuel ratio sensor concerning a second embodiment of the present disclosure.
Figure 6:
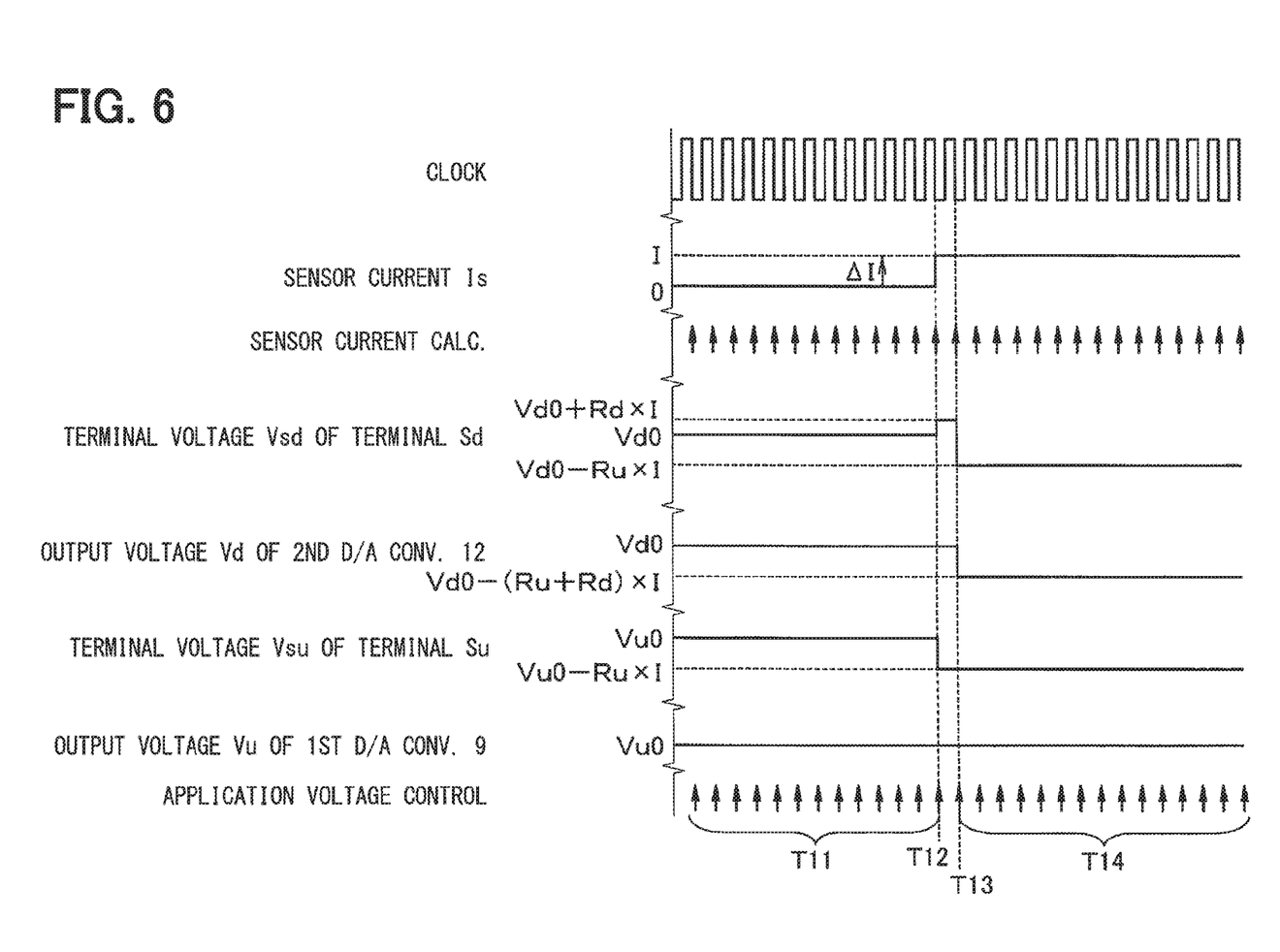
FIG. 6 is a timing chart of an operation of the controller in the second embodiment of the present disclosure.

FIGS. 5 and 6 show a block diagram and a timing chart of the second embodiment of the present disclosure, as the additional explanation.

In the second embodiment, a voltage application scheme is that (i) a constant voltage is applied to the terminal Su on the upstream side, and (ii) a variable voltage is applied to the terminal Sd on the downstream side.

A digital processor 103 which replaces the digital processor 3 has an adjuster 114, a calculator 115, and a control unit 116, and the control unit 116 is provided with a memory 118.

The adjuster 114 sets the first input digital value inputted to the first D/A converter 9 as a constant value so that a voltage of the terminal Su is adjusted to a preset voltage Vout (=Vsu). The constant value is inputted also to the control unit 116.

The calculator 115 calculates the sensor current Is according to the above-mentioned equation (2), and provides the calculated sensor current Is as the feedback output 17 of the air-fuel ratio, and outputs the calculated sensor current Is to the control unit 116.

The control unit 116 outputs the second input digital value of the second D/A converter 12 as an instruction value based on the constant value inputted from the adjuster 114 and the digital value of the sensor current Is.

When the target voltage applied to the air-fuel ratio sensor 2 is set to Vtar the control unit 116 calculates the output voltage Vd of the second D/A converter 12 according to a following equation (1b), and controls the second input digital value of the second D/A converter 12 to correspond to the output voltage Vd.

$$Vd = Vout - \{Vtar + Is \times (Rd + Ru)\} \qquad \text{Equation (1b)}$$

Resistance Rd+Ru of the equation (1b) is equivalent to a sum of resistances along the path between the output of the first voltage application circuit 4 and the output of the second voltage application circuit 5, except for the resistance caused by an impedance Z of the air-fuel ratio sensor 2.

The operation of the controller 101 is described with reference to FIG. 6 in connection with the feature of the present embodiment based on the above-mentioned composition. The focus of the following description is also put on the point of how the feature control of the present embodiment is performed at the electric current change timing. The digital processor 103 calculates the sensor current Is at the edge generation timing of the clock signal, and controls the application voltage to the air-fuel ratio sensor 2 immediately after calculating the sensor current Is. The sensor current calculation process and the application voltage control process are respectively performed at every edge generation timing of the clock signal.

During a normal operation time, based on an assumption that the air-fuel ratio is taking a stoichiometric value (i.e., a theoretical air-fuel ratio), the electric current that flows in the air-fuel ratio sensor 2 is 0 [mA], and the sensor current Is also becomes 0 [mA].

As shown in a period T11, when there is no change of the sensor current Is, the control unit 116 does not change the application voltage Vsd to the output the terminal Sd from the preset voltage Vd0 (e.g., 2.5 [V]), and does not change the application voltage Vsu to the output the terminal Su from the voltage Vu0 (e.g., 2.9 [V]). Thereby, the application voltage Vsu−Vsd to the air-fuel ratio sensor 2 is controlled to the target voltage Vtar, i.e., to a constant voltage Vu0−Vd0.

For example, at a certain timing T12, when the change ΔI of the sensor current is caused under an influence of unknown factor (e.g., environmental temperature change), the change ΔI of the sensor current may cause an influence on the voltage drop of the resistor 11 and the voltage drop of the sensing resistor 6, and the terminal voltage Vsd of the terminal Sd changes to Vd0+Rd×I at timing T12, and the terminal voltage Vsu of the terminal Su changes to Vu0−Ru×I.

Then, the control unit 116 of the digital processor 103 changes the application voltage Vsd of the terminal Sd on the downstream side at the next clock timing T13, when a change of the sensor current Is calculated by the calculator 115 is detected.

At timing T13, as shown in the above-mentioned equation (1b), a downward change of the application voltage Vd on the downstream side is performed by an amount I×(Ru+Rd).

Thereby, in consideration of the influence of the voltage drop by the resistor 11, the air-fuel ratio sensor 2, and the current sensing resistor 6, the application voltage Vsd to the terminal Sd on the downstream side is changed to Vd0−Ru×I.

As a result, the application voltage Vsu−Vsd to the air-fuel ratio sensor 2 is controllable to the constant voltage Vu0−Vd0.

Then, as shown in a period T14, the control unit 116 maintains the application voltage Vsd if the sensor current Is does not change from the current value I.

As explained above, the same operation effects as the above-mentioned embodiment are achieved by the present embodiment.

Third Embodiment

Figure 7:
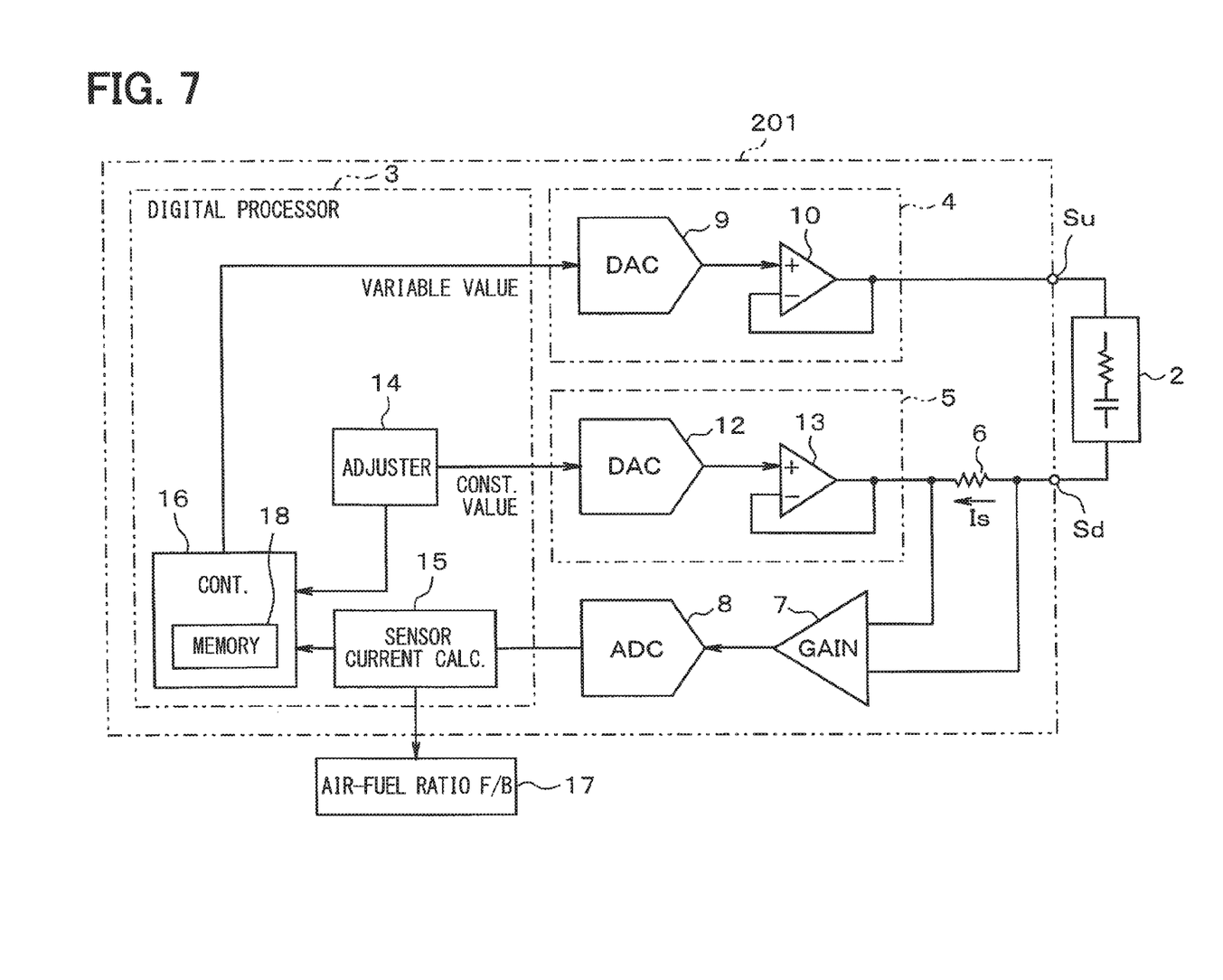
FIG. 7 is a block diagram of an electric configuration of the controller of the air-fuel ratio sensor concerning a third embodiment of the present disclosure.

FIG. 7 shows, as the additional explanation, a block diagram of the third embodiment of the present disclosure.

A motor controller 201 shown in FIG. 7 corresponds to a block diagram of the controller 1 in FIG. 1 of the first embodiment, with a difference therefrom of dispensing the protection resistor 11. That is, an application of the present embodiment to the motor controller 201 is a case where Ru in the above-described equation (1a) is set to 0 (i.e., Ru=0). Therefore, in the present embodiment, the equation (1a) is replaced with the following equation (1c).

$$Vu = Vout + (Vtar + Is \times Rd) \quad \text{Equation (1c)}$$

Therefore, just like the first embodiment, when the change ΔI is caused, the application voltage on the upstream side is raised, i.e., the upward change for the application voltage is performed, by an amount of I×Rd. In such manner, the application voltage Vsu to the terminal Su on the upstream side is controlled to Vu0, and the application voltage Vsu Vsd to the air-fuel ratio sensor 2 is controlled to the constant voltage Vu0−Vd0.

Since other factors are the same as the first embodiment, description regarding other factors is omitted.

The same operation effects as the above-mentioned embodiments are achieved by the present embodiment.

Fourth Embodiment

Figure 8:
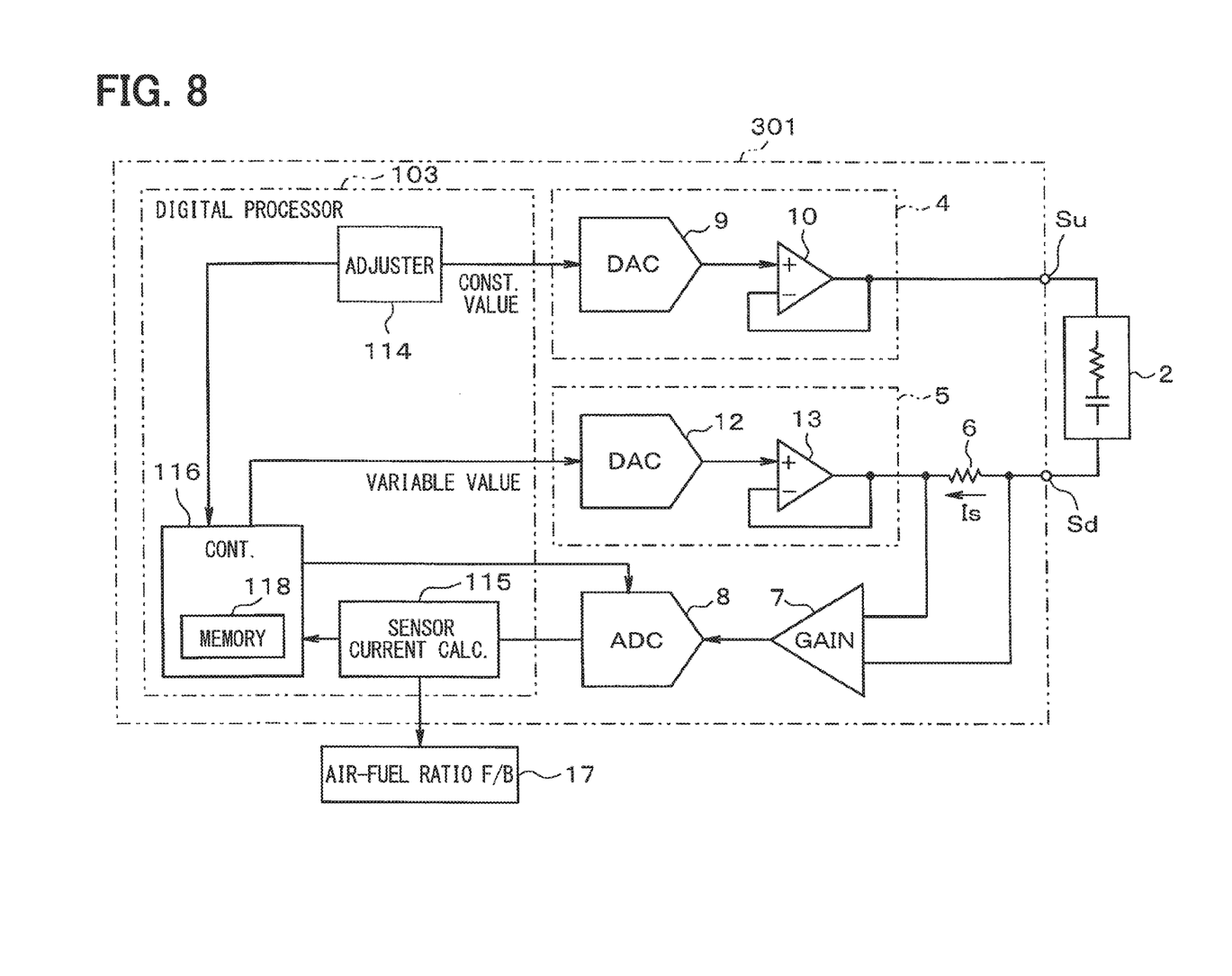
FIG. 8 is a block diagram of an electric configuration of the controller of the air-fuel ratio sensor concerning a fourth embodiment of the present disclosure.

FIG. 8 shows, as the additional explanation, a block diagram in the fourth embodiment of the present disclosure.

A motor controller 301 shown in FIG. 8 corresponds to a block diagram of the controller 101 in FIG. 5 of the second embodiment, with a difference therefrom of dispensing the protection resistor 11. That is, an application of the present embodiment to the motor controller 301 is interpreted as a case where Ru in the above-described equation (1b) is set to 0 (i.e., Ru=0). Therefore, in the present embodiment, the equation (1b) is replaced with the following equation (1d).

$$Vd = Vout - (Vtar + Is \times Rd) \quad \text{Equation (1d)}$$

Therefore, just like the second embodiment, when the change ΔI is caused, the application voltage on the downstream side is raised, i.e., the downward change for the application voltage is performed, by an amount of I×Rd. In such manner, the application voltage Vsd to the terminal Sd on the downstream side is controlled to Vd0, and the application voltage Vsu−Vsd to the air-fuel ratio sensor 2 is controlled to the constant voltage Vu0−Vd0.

Since other factors are the same as the first embodiment, description regarding other factors is omitted.

The same operation effects as the above-mentioned embodiment are achieved by the present embodiment.

Fifth Embodiment

Figure 9:
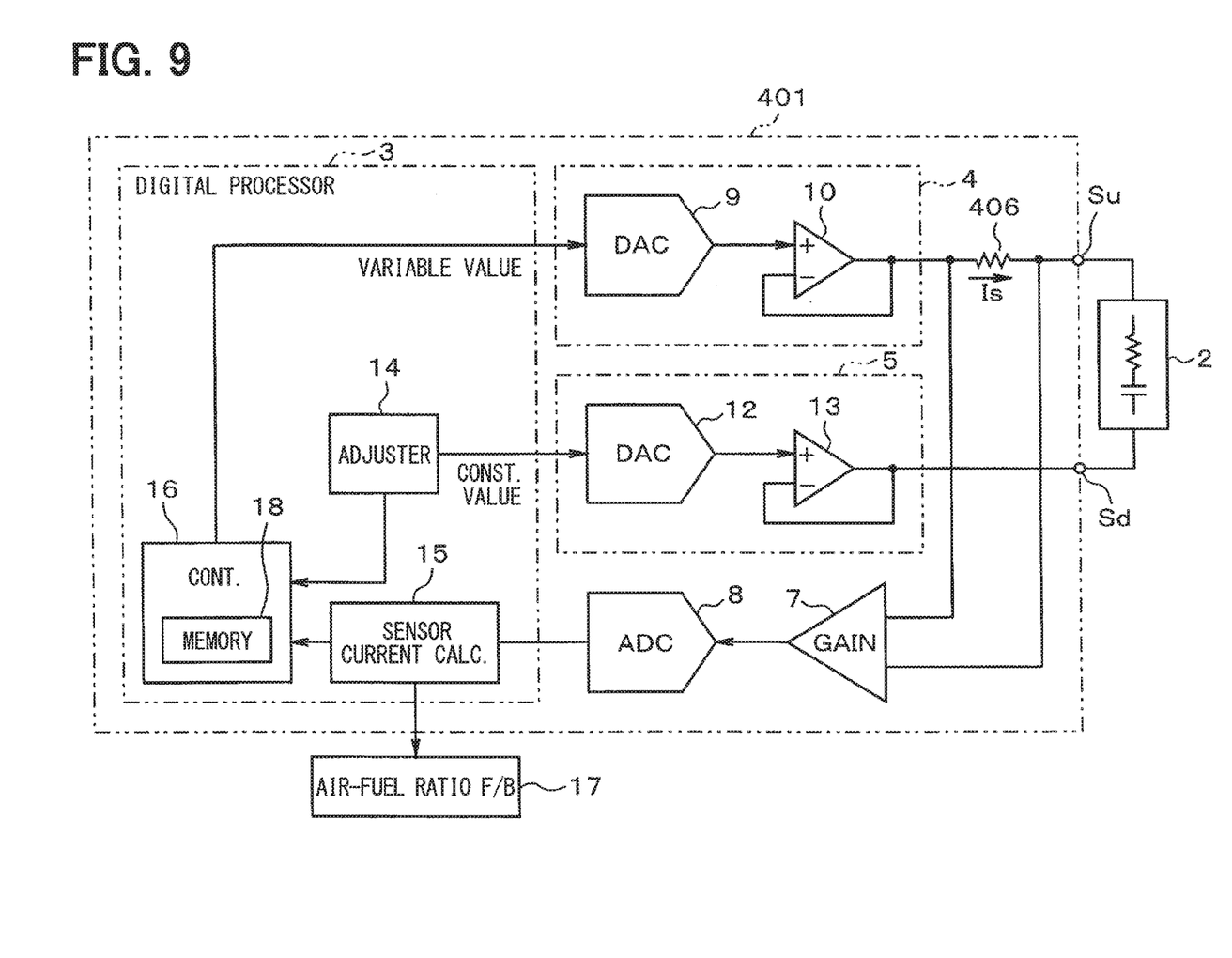
FIG. 9 is a block diagram of an electric configuration of the controller of the air-fuel ratio sensor concerning a fifth embodiment of the present disclosure.

FIG. 9 shows, as the additional explanation, a block diagram in the fifth embodiment of the present disclosure.

A motor controller 401 shown in FIG. 9 corresponds to a block diagram of the controller 1 in FIG. 1 of the first embodiment, and also corresponds to a block diagram in FIG. 7 regarding the third embodiment.

A difference of the present embodiment from the first and third embodiments is that, (i) a resistor 406 is disposed, as a series connection component, at a position between the output terminal of the first operational amplifier 10 of the first voltage application circuit 4 and the terminal Su on the upstream side, i.e., as a current sensing resistor, and (ii) a protection resistor is not provided just like the third embodiment.

In the circuit configuration of the present embodiment, the resistor 406 and the air-fuel ratio sensor 2 are provided at an interposing position between the first voltage application circuit 4 and the second voltage application circuit 5, which is the same configuration as the third embodiment.

Therefore, by performing a control according to the equation (1a), or according to the equation (1c), or according to the similar equation, the target voltage Vtar is controlled to a constant value, i.e. to the voltage Vu0−Vd0. Details of such control are the same as the above-described embodiments.

The same operation effects as the above-mentioned embodiments are achieved by the present embodiment.

Sixth Embodiment

Figure 10:
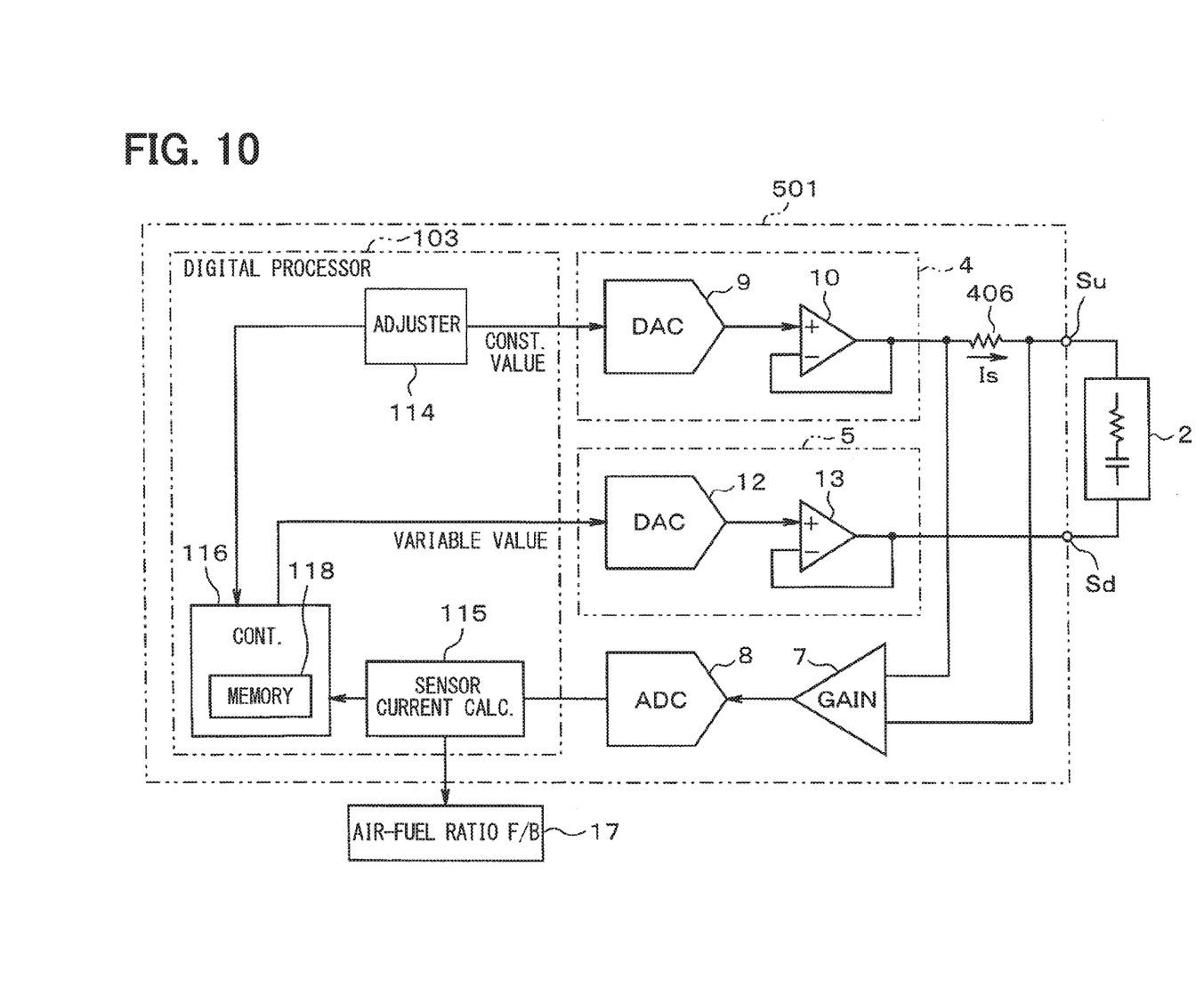
FIG. 10 is a block diagram of an electric configuration of the controller of the air-fuel ratio sensor concerning a sixth embodiment of the present disclosure.

FIG. 10 shows, as the additional explanation, a block diagram in the sixth embodiment of the present disclosure.

A controller 501 shown in FIG. 10 corresponds to a block diagram of the controller 101 in FIG. 5 of the second embodiment, and also corresponds to a block diagram of the controller 301 in FIG. 8 of the fourth embodiment.

A difference of the present embodiment from the second and fourth embodiments is that (i) a resistor 406 is disposed, as a series connection component, at a position between the output terminal of the first operational amplifier 10 of the first voltage application circuit 4 and the terminal Su on the upstream side, i.e., as a current sensing resistor, and (ii) a protection resistor is not provided just like the third embodiment.

In the circuit configuration of the present embodiment, the resistor 406 and the air-fuel ratio sensor 2 are provided at an interposing position between the first voltage application circuit 4 and the second voltage application circuit 5, which is the same configuration as the fourth embodiment.

Therefore, by performing a control according to the equation (1b), or according to the equation (1d), or according to the similar equation, the target voltage Vtar is controlled to a constant value, i.e. to the voltage Vu0−Vd0. Details of such control are the same as the above-described embodiments.

The same operation effects as the above-mentioned embodiments are achieved by the present embodiment.

Seventh Embodiment

Figure 11:
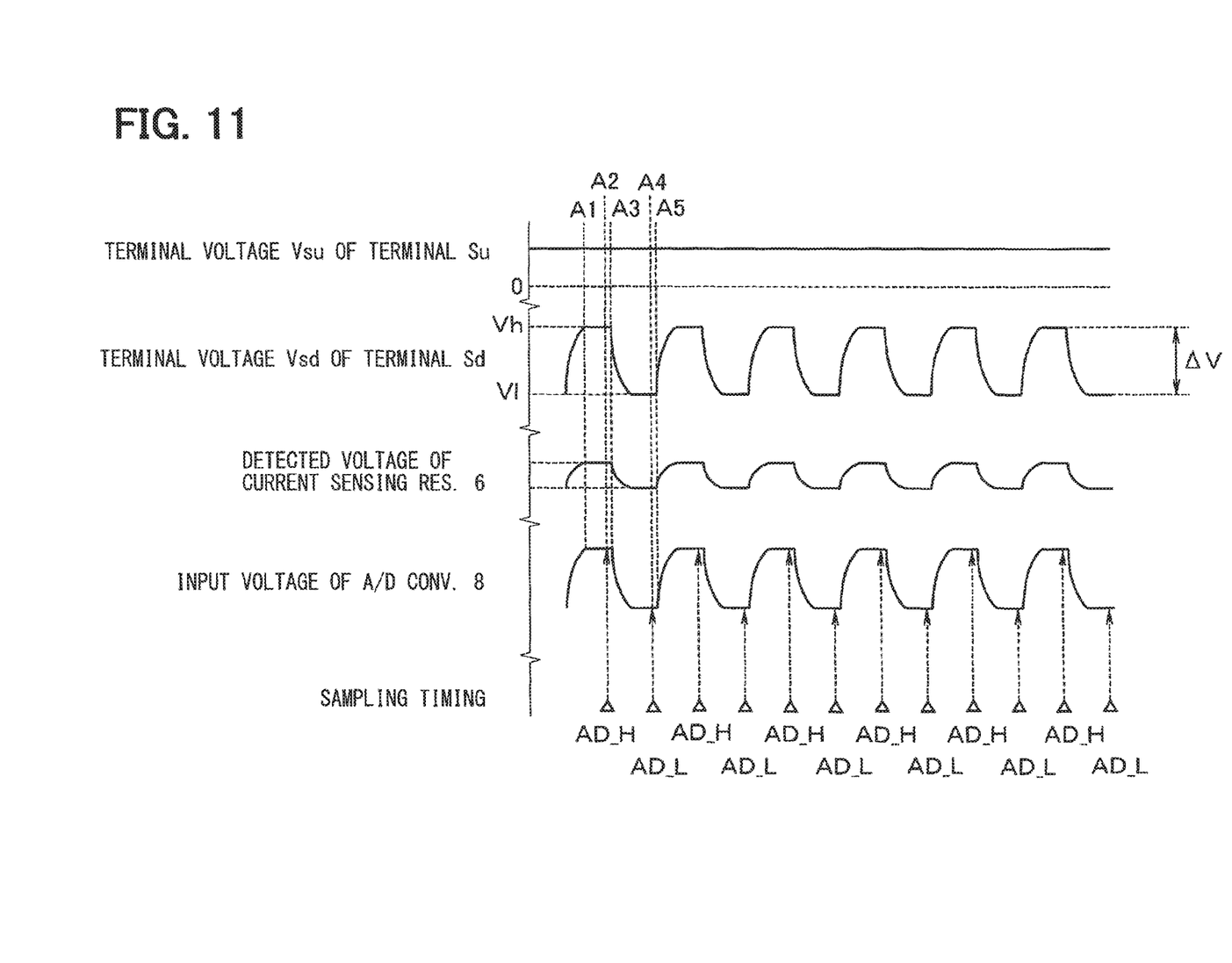
FIG. 11 is a timing chart of an operation concerning a seventh embodiment of the present disclosure.

FIG. 11 shows, as the additional explanation, a timing chart of the seventh embodiment of the present disclosure.

In the seventh embodiment, the control unit 16 changes the voltage of the terminal Sd on the downstream side in a stepwise manner, or in a continuous manner, and, during such change of the voltage, the A/D conversion voltage is sampled by the A/D converter 8 for the calculation of the sensor current is or the impedance Z based on a series of plural sampling voltages (e.g., sampled voltages from two successive points/sampling timings). Such a feature of the present embodiment is described in the following in more details.

In the present embodiment, the circuit configuration is borrowed from FIG. 8, for example, and the voltage of each node is changeable as shown in FIG. 11. Thus, the configuration of FIG. 8 is used as a basic assumption.

In FIG. 8, the adjuster 114 outputs the first input digital value to the first D/A converter 9 as a constant value, and the control unit 116 inputs the second input digital value to the second D/A Converter 12 as a variable value.

During such time, a sweeping change is caused in the second input digital value by the control unit 116, for the input of the second input digital value to the second D/A converter 12. A range of the sweeping change of the voltage Vsd on the terminal Sd is designated as ΔV.

The input voltage to the A/D converter 8 changes in proportion to the voltage between the two terminals of the current sensing resistor 6. Therefore, when the control unit 116 inputs the second input digital value to the second D/A converter 12 as a variable value, the input voltage to the A/D converter 8 also changes in a corresponding manner to the variation of the second input digital value.

FIG. 11 shows a timing chart of the sampling timings together with the voltage of each node.

For example, the control unit 116 inputs the second input digital value to the second D/A converter 12, for example, so that the voltage of the terminal Sd is changed in two levels, i.e., to a high voltage Vh and to a low voltage Vl that is lower than the high voltage Vh, in a rectangular wave form or in an alternating wave form. For such control, the control unit 116 inputs the second input digital value for inputting the high voltage Vh at timing A1 to the second D/A converter 12.

Then, the control unit 116 controls the A/D converter 8 to sample the input voltage at timing A2, which is assumed to reserve a sufficient period of convergence, or settlement, after the input of the high voltage Vh. The A/D-conversion value of the A/D converter 8 at such timing is calculated as a value "AD_H."

Then, the control unit 116 changes the second input digital value for inputting the low voltage Vl at timing A3, and inputs the changed second input digital value to the second D/A converter 12.

Then, the control unit 116 controls the A/D converter 8 to sample the input voltage at timing A4, which is assumed to reserve a sufficient period of convergence, or settlement, after the input of the low voltage Vl. The A/D-conversion value of the A/D converter 8 at such timing is calculated as a value "AD_L."

Then, the control unit 116 changes the second input digital value for inputting the high voltage Vh at timing A5, and inputs the changed second input digital value to the second D/A converter 12.

Such a process is repeatedly performed.

The calculator 115 calculates the sensor current Is and/or the impedance Z of the air-fuel ratio sensor 2 by using the value AD_H and the value AD_L of the A/D converter 8 obtained at the sampling timings. When the calculator 115 calculates the sensor current Is, the following equation (3) is used.

$$Is=(AD\_H+AD\_L)/(2 \times G \times Rd) \qquad \text{Equation (3)}$$

The value Is is derived from a division of an average voltage (AD_H+AD_L)/2 by the gain G and the resistance Rd of the current sensing resistor 6.

When the calculator 115 calculates the impedance Z of the air-fuel ratio sensor 2, it is calculated based on a voltage difference (AD_H−AD_L). The calculator 115 calculates the impedance Z of the air-fuel ratio sensor 2 based on the following equation (4), for example.

$$X=\{G \times \Delta V - (AD\_H - AD\_L)\} \times Rd/(AD\_H - AD\_L) \qquad \text{Equation (4)}$$

The equation (4) is derived from the following equations (5)-(7).

In the following equations (5)-(7), an electric current Ih is an electric current that flows in the air-fuel ratio sensor 2 when the high voltage Vh is applied to the terminal Sd, and an electric current Il is an electric current that flows in the air-fuel ratio sensor 2 when the low voltage Vl is applied to the terminal Sd.

$$G \times Rd \times Ih = AD\_H \qquad \text{Equation (5)}$$

$$G \times Rd \times Il = AD\_L \qquad \text{Equation (6)}$$

$$Z \times Ih + Rd \times Ih(Z \times Il + Rd \times Il) = \Delta V \qquad \text{Equation (7)}$$

Since the gain G of the amplifier, the voltage difference ΔV, and the resistance Rd of the resistor 6 are all predetermined values, the impedance Z of the air-fuel ratio sensor 2 is calculable based on the above-mentioned equation (4). More specifically, the impedance Z of the air-fuel ratio sensor 2 is calculable substantially in real time, in general, by calculating the impedance Z by using the A/D-conversion values AD_H and AD_L from two successive sampling timings.

Thereby, the calculated impedance Z of the air-fuel ratio sensor 2 is usable for the feedback control.

OTHER EMBODIMENTS

Although the present disclosure has been described in connection with preferred embodiment thereof with reference to the accompanying drawings, it is to be noted that various changes and modifications will become apparent to those skilled in the art.

Although the digital processors 3 and 103 in the above-described embodiments are described as providing the target voltage Vtar of the application voltage applied to the air-fuel ratio sensor 2 as a constant value, such a configuration may be modified.

For example, as shown by a load line 20, i.e., a line (b) of FIG. 2, the digital processors 3 and 103 may change the target voltage Vtar applied to the air-fuel ratio sensor 2 according to the sensor current Is detected by the current sensing resistors 6 and 406 (e.g., a change may be proportional to the sensor current Is).

Although the digital processors 3 and 103 are described as a DSP in the above-described embodiments, the digital processors 3 and 103 may be a device other than the DSP.

Such changes, modifications, and summarized schemes are to be understood as being within the scope of the present disclosure as defined by appended claims.

What is claimed is:

1. A controller of an air-fuel ratio sensor for controlling and outputting a first application voltage to a first terminal of the air-fuel ratio sensor and a second application voltage to a second terminal of the air-fuel ratio sensor, the controller comprising:
- a first voltage application circuit having
  - a first Digital-to-Analog (D/A) converter that converts a first input digital value and outputs an analog voltage, and
  - a first operational (OP) amplifier configured to receive the analog output voltage from the first D/A converter at a non-inverted input terminal, and to output a voltage from an output terminal, wherein the voltage output from the first OP amplifier is directly input into an inverted input terminal of the first OP amplifier and input to the first terminal of the air-fuel ratio sensor;
- a second voltage application circuit having
  - a second D/A converter that converts a second input digital value and outputs an analog voltage, and
  - a second operational (OP) amplifier configured to receive the analog output voltage from the second D/A converter at a non-inverted input terminal, and to output a voltage from an output terminal, wherein the voltage output from the second OP amplifier is directly input into an inverted input terminal of the second OP amplifier and input to the second terminal of the air-fuel ratio sensor;
- a current sensing resistor having a resistance value and disposed at a position between the output terminal of the first OP amplifier and the output terminal of the second OP amplifier, the current sensing resistor for sensing a sensor current (Is) that flows in the air-fuel ratio sensor;
- an Analog-to-Digital (A/D) converter configured to receive a voltage across the current sensing resistor as an input, to convert the voltage across the current sensing resistor by an A/D conversion, and to output a digital value; and
- a digital processor configured to receive the digital value output from the A/D converter and to output the first input digital value to the first D/A converter and the second input digital value to the second D/A converter based on the digital value from the A/D converter,
- wherein the digital processor includes:
  - an adjuster configured to adjust the second input digital value to adjust the voltage output from the second OP amplifier to a preset voltage;
  - a calculator configured to calculate a digital value of the sensor current flowing in the current sensing resistor based on a ratio of the digital value output by the A/D converter to the resistance value of the current sensing resistor; and
  - a control unit configured to control the first input digital value based on a calculation result of the calculator for controlling the output voltage of the first OP amplifier as a voltage $V_u$ based on an equation $V_u = V_{out} \pm (V_{tar} + I_s \times R_s)$,
  - wherein $V_{tar}$ is a target voltage applied to the air-fuel ratio sensor, $I_s$ is the sensor current, $R_s$ is the resistance value of the current sensing resistor, $(V_{tar} + I_s \times R_s)$ is an adjusting factor, and $V_{out}$ is the preset voltage;
  - wherein the adjusting factor is added to the preset voltage when the voltage output from the first OP amplifier is applied to the first terminal of the air-fuel ratio sensor and the voltage output from the second OP amplifier is applied to the second terminal of the air-fuel ratio sensor; and
  - wherein the adjusting factor is subtracted from the preset voltage when the voltage output from the first OP amplifier is applied to the second terminal of the air-fuel ratio sensor and the voltage output from the second OP amplifier is applied to the first terminal of the air-fuel ratio sensor.

2. The controller of the air-fuel ratio sensor of claim 1, further comprising
- a protection resistor having a resistance value is disposed at a position between the first terminal of the air-fuel ratio sensor and the output terminal of the first OP amplifier, when the current sensing resistor is disposed at a position between the second terminal of the air-fuel ratio sensor and the output terminal of the second OP amplifier,
- wherein the digital processor is further configured to control the voltage output from the first OP amplifier as the voltage $V_u$ based on an equation $V_u = V_{out} \pm \{V_{tar} + I_s \times (R_s + R_p)\}$,
- wherein $R_p$ is the resistance value of the protection resistor, and
- wherein the resistance value $R_p$ of the protection resistor is added to the resistance value $R_s$ of the current sensing resistor.

3. The controller of the air-fuel ratio sensor of claim 1, wherein the digital processor is further configured to provide the target voltage as a constant voltage.

4. The controller of the air-fuel ratio sensor of claim 1, wherein the digital processor is further configured to change the target voltage based on the sensor current ($I_s$) detected by the current sensing resistor.

5. The controller of an air-fuel ratio sensor of claim 1, wherein the digital processor is further configured to calculate the sensor current flowing in the air-fuel ratio sensor or an impedance of the air-fuel ratio sensor (i) by performing a sweep change of the application voltage applied to the air-fuel ratio sensor, and (ii) by collecting plural sampling voltages during the sweep change.

* * * * *